US008415329B1

(12) United States Patent
Mishra

(10) Patent No.: US 8,415,329 B1
(45) Date of Patent: Apr. 9, 2013

(54) THERMOPROTECTED COMPOSITIONS AND PROCESS FOR TERMINAL STEAM STERILIZATION OF MICROPARTICLE PREPARATIONS

(75) Inventor: Awadhesh K. Mishra, Quebec (CA)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 09/321,766

(22) Filed: May 28, 1999

Related U.S. Application Data

(60) Provisional application No. 60/087,331, filed on May 29, 1998.

(51) Int. Cl.
*A61K 31/66* (2006.01)
*A61K 31/70* (2006.01)

(52) U.S. Cl.
USPC ............................................. 514/75; 514/23

(58) Field of Classification Search .................. 424/405, 424/400, 489; 514/937, 975, 23, 75
See application file for complete search history.

(56) References Cited

U.S. PATENT DOCUMENTS

| | | |
|---|---|---|
| 2,803,582 A | 8/1957 | Cherney |
| 3,137,631 A | 6/1964 | Soloway |
| 3,216,897 A | 11/1965 | Krantz, Jr. |
| 3,274,063 A | 9/1966 | Nieper et al. |
| 3,594,476 A | 7/1971 | Merrill |
| 3,715,432 A | 2/1973 | Merrill |
| 3,755,557 A | 8/1973 | Jacobs |
| 3,794,476 A | 2/1974 | Michalik et al. |
| 3,937,668 A | 2/1976 | Zolle |
| 3,960,757 A | 6/1976 | Morishita et al. |
| 3,965,255 A | 6/1976 | Bloch et al. |
| 4,016,100 A | 4/1977 | Suzuki et al. |
| 4,053,585 A | 10/1977 | Allison et al. |
| 4,056,635 A | 11/1977 | Glen et al. |
| 4,073,943 A | 2/1978 | Wretlind et al. |
| 4,078,052 A | 3/1978 | Papahadjopoulos |
| 4,089,801 A | 5/1978 | Schneider |
| 4,102,806 A | 7/1978 | Kondo et al. |
| 4,107,288 A | 8/1978 | Oppenheim et al. |
| 4,133,874 A | 1/1979 | Miller et al. |
| 4,145,410 A | 3/1979 | Sears |
| 4,147,767 A | 4/1979 | Yapel, Jr. |
| 4,186,183 A | 1/1980 | Steck et al. |
| 4,219,548 A | 8/1980 | Reller |
| 4,235,871 A | 11/1980 | Papahadjopoulos et al. |
| 4,241,046 A | 12/1980 | Papahadjopoulos et al. |
| 4,271,196 A | 6/1981 | Schmidt |
| 4,298,594 A | 11/1981 | Sears et al. |
| 4,302,459 A | 11/1981 | Steck et al. |
| 4,308,166 A | 12/1981 | Marchetti et al. |
| 4,309,421 A | 1/1982 | Ghyczy et al. |
| 4,316,884 A | 2/1982 | Alam et al. |
| 4,320,121 A | 3/1982 | Sears |
| 4,325,871 A | 4/1982 | Sasaki et al. |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |
| 4,332,796 A | 6/1982 | Los |
| 4,340,594 A | 7/1982 | Mizushima et al. |
| 4,345,588 A | 8/1982 | Widder et al. |
| 4,351,831 A | 9/1982 | Growdon et al. |
| 4,356,167 A | 10/1982 | Kelly |
| 4,369,182 A | 1/1983 | Ghyczy et al. |
| 4,371,516 A | 2/1983 | Gregory et al. |
| 4,378,354 A | 3/1983 | Ghyczy et al. |
| 4,394,372 A | 7/1983 | Taylor |
| 4,397,846 A | 8/1983 | Weiner et al. |
| 4,411,894 A | 10/1983 | Schrank et al. |
| 4,411,933 A | 10/1983 | Samejima et al. |
| 4,421,747 A | 12/1983 | Ghyczy et al. |
| 4,427,649 A | 1/1984 | Dingle et al. |
| 4,432,975 A | 2/1984 | Libby |
| 4,448,765 A | 5/1984 | Ash et al. |
| 4,483,847 A | 11/1984 | Augart |
| 4,485,054 A | 11/1984 | Mezei et al. |
| 4,492,720 A | 1/1985 | Mosier |
| 4,515,736 A | 5/1985 | Deamer |
| 4,529,561 A | 7/1985 | Hunt et al. |
| 4,532,089 A | 7/1985 | MacDonald |
| 4,610,868 A | 9/1986 | Fountain et al. |
| 4,613,505 A | 9/1986 | Mizushima et al. |

(Continued)

FOREIGN PATENT DOCUMENTS

| | | |
|---|---|---|
| DE | 2 513 797 | 10/1975 |
| DE | 2 938 807 | 11/1980 |

(Continued)

OTHER PUBLICATIONS

"Nanosuspensionen", AK Kayser, Institut für Pharmazie, http://userpage.fu-berlin.de, Nov. 20, 2000 (web date).
R.H. Müller, K. Peters, R. Becker and B. Kruss, "Nanosuspensions for the I.V. Administration of Poorly Soluble Drugs—Stability During Sterilization and Long-Term Storage", Proc. Int. Symp. Control Rel. Bioact. Mater., 22, 574-575 (1995).
Zuidam et al., "Sterilization of Liposomes by Heat Treatment", Plenum Publishing Corp., Pharmaceutical Reserch vol. 10, No. 11, 1591-96 (1993).
International Search Report for corresponding PCT International Application No. PCT/US99/11888. (3 sheets).
Ross et al., "Aqueous Solutions of Surface-Active Solutes", *Collodial Systems and Interfaces*, © 1988, pp. 148-151.
Sande et al., "Antimicrobial Agents: Antifungal and Antiviral Agents", pp. 1219-1222.
Bittman, Robert, "Sterol-Polyene Antibiotic Complexation: Probe of Membrane Structure," *Lipids*, vol. 13, No. 10, pp. 686-691 (1978).
Mishra et al., "Scientifically Speaking: Novel Injectable Formulations of Water-Insoluble Drugs", *Controlled Release Newsletter*, vol. 17, Issue 2, (Jun. 2000), pp. 21-30.

(Continued)

*Primary Examiner* — Zohreh Fay
(74) *Attorney, Agent, or Firm* — Mintz Levin Cohn Ferris Glovsky and Popeo, P.C.; Muriel Liberto, Esq.

(57) ABSTRACT

Compositions of submicron- to micron-sized particles of water-insoluble biologically active substances that are stabilized by thermoprotecting agents, can be terminally steam sterilized without any significant increase of mean particle size. These compositions display markedly reduced heat-induced coagulation, flocculation, or particle size growth during the terminal steam sterilization process.

23 Claims, No Drawings

U.S. PATENT DOCUMENTS

| | | | |
|---|---|---|---|
| 4,622,219 A | | 11/1986 | Haynes |
| 4,629,626 A | * | 12/1986 | Miyata et al. |
| RE32,393 E | | 4/1987 | Wretland et al. |
| 4,675,236 A | | 6/1987 | Ohkawara et al. |
| 4,687,762 A | | 8/1987 | Fukushima et al. |
| 4,725,442 A | | 2/1988 | Haynes |
| 4,756,910 A | | 7/1988 | Yagi et al. |
| 4,758,598 A | | 7/1988 | Gregory |
| 4,761,288 A | | 8/1988 | Mezei |
| 4,762,720 A | | 8/1988 | Jizomoto |
| 4,766,046 A | | 8/1988 | Abra et al. |
| 4,776,991 A | | 10/1988 | Farmer et al. |
| 4,800,079 A | | 1/1989 | Boyer |
| 4,801,455 A | | 1/1989 | List et al. |
| 4,803,070 A | | 2/1989 | Cantrell et al. |
| 4,806,350 A | | 2/1989 | Gerber |
| 4,806,352 A | | 2/1989 | Cantrell |
| 4,826,687 A | | 5/1989 | Nerome et al. |
| 4,839,111 A | | 6/1989 | Huang |
| 4,880,634 A | | 11/1989 | Speiser |
| 4,895,726 A | | 1/1990 | Curtet et al. |
| 4,961,890 A | | 10/1990 | Boyer |
| 4,963,367 A | | 10/1990 | Ecanow |
| 4,973,465 A | | 11/1990 | Baurain et al. |
| 4,990,337 A | | 2/1991 | Kurihara et al. |
| 5,030,453 A | | 7/1991 | Lenk et al. |
| 5,091,187 A | | 2/1992 | Haynes et al. |
| 5,091,188 A | | 2/1992 | Haynes |
| 5,100,591 A | | 3/1992 | Leclef et al. |
| 5,145,684 A | | 9/1992 | Liversidge et al. |
| 5,164,380 A | | 11/1992 | Carli et al. |
| 5,169,847 A | | 12/1992 | Nagy née Kricsfalussy et al. |
| 5,179,079 A | | 1/1993 | Hansen et al. |
| 5,217,707 A | | 6/1993 | Szabo et al. |
| 5,246,707 A | | 9/1993 | Haynes |
| 5,272,137 A | | 12/1993 | Blasé et al. |
| 5,298,262 A | | 3/1994 | Na et al. |
| 5,302,401 A | | 4/1994 | Liversidge et al. |
| 5,304,564 A | | 4/1994 | Tsuboi et al. |
| 5,320,906 A | | 6/1994 | Eley et al. |
| 5,326,552 A | | 7/1994 | Na et al. |
| 5,336,507 A | | 8/1994 | Na et al. |
| 5,340,564 A | | 8/1994 | Illig et al. |
| 5,346,702 A | | 9/1994 | Na et al. |
| 5,352,459 A | | 10/1994 | Hollister et al. |
| 5,360,593 A | * | 11/1994 | Bapatla |
| 5,364,633 A | | 11/1994 | Hill et al. |
| 5,389,377 A | | 2/1995 | Chagnon et al. |
| 5,399,363 A | | 3/1995 | Liversidge et al. |
| 5,447,710 A | | 9/1995 | Na et al. |
| 5,470,583 A | | 11/1995 | Na et al. |
| 5,510,118 A | | 4/1996 | Bosch et al. |
| 5,527,537 A | | 6/1996 | Dietl |
| 5,545,628 A | | 8/1996 | Deboeck et al. |
| RE35,338 E | | 9/1996 | Haynes |
| 5,552,160 A | | 9/1996 | Liversidge et al. |
| 5,560,931 A | | 10/1996 | Eickhoff et al. |
| 5,569,448 A | | 10/1996 | Wong et al. |
| 5,571,536 A | | 11/1996 | Eickhoff et al. |
| 5,576,016 A | | 11/1996 | Amselem et al. |
| 5,578,325 A | | 11/1996 | Domb et al. |
| 5,589,455 A | | 12/1996 | Woo |
| 5,603,951 A | | 2/1997 | Woo |
| 5,631,023 A | | 5/1997 | Kearney et al. |
| 5,637,625 A | | 6/1997 | Haynes |
| 5,639,474 A | | 6/1997 | Woo |
| 5,645,856 A | | 7/1997 | Lacy et al. |
| 5,656,289 A | | 8/1997 | Cho et al. |
| 5,660,858 A | | 8/1997 | Parikh et al. |
| 5,662,932 A | | 9/1997 | Amselem et al. |
| 5,663,198 A | | 9/1997 | Reul et al. |
| 5,676,928 A | | 10/1997 | Klaveness et al. |
| 5,739,152 A | * | 4/1998 | Andersson et al. |
| 5,776,491 A | | 7/1998 | Allen, Jr. et al. |
| 5,776,495 A | | 7/1998 | Duclos et al. |
| 5,827,536 A | | 10/1998 | Laruelle |
| 5,827,822 A | | 10/1998 | Floc'h et al. |
| 5,834,025 A | | 11/1998 | de Garavilla et al. |
| 5,851,275 A | | 12/1998 | Amidon et al. |
| 5,858,398 A | | 1/1999 | Cho |
| 5,858,410 A | | 1/1999 | Muller et al. |
| 5,880,148 A | | 3/1999 | Edgar et al. |
| 5,922,355 A | | 7/1999 | Parikh et al. |
| 5,932,243 A | | 8/1999 | Fricker et al. |
| 5,972,366 A | | 10/1999 | Haynes et al. |
| 5,976,577 A | | 11/1999 | Green et al. |
| 6,045,829 A | | 4/2000 | Liversidge et al. |
| 6,046,163 A | | 4/2000 | Stuchlik et al. |
| 6,057,289 A | | 5/2000 | Mulye |
| 6,063,762 A | | 5/2000 | Hong et al. |
| 6,086,376 A | | 7/2000 | Moussa et al. |
| 6,096,338 A | | 8/2000 | Lacy et al. |
| 6,228,399 B1 | | 5/2001 | Parikh et al. |
| 6,267,989 B1 | | 7/2001 | Liversidge et al. |
| 6,270,806 B1 | | 8/2001 | Liversidge et al. |
| 6,337,092 B1 | | 1/2002 | Khan et al. |
| 6,387,409 B1 | | 5/2002 | Khan et al. |

FOREIGN PATENT DOCUMENTS

| | | |
|---|---|---|
| DE | 3 421 468 | 12/1985 |
| DE | 44 40 337 A1 | 5/1996 |
| DE | 4440337 A | 5/1996 |
| EP | 0 052 322 | 5/1982 |
| EP | 0 193 208 | 9/1986 |
| EP | 0 272 091 | 6/1988 |
| EP | 0 330 532 | 8/1989 |
| EP | 0 391 369 | 10/1990 |
| EP | 0 418 153 | 3/1991 |
| EP | 0 456 670 | 11/1991 |
| EP | 0 456 764 | 11/1991 |
| EP | 0 499 299 | 8/1992 |
| EP | 0 570 829 | 5/1993 |
| EP | 0 580 690 | 2/1994 |
| EP | 0 601 618 A2 | 6/1994 |
| EP | 0 602 700 | 6/1994 |
| EP | 687 172 | 12/1995 |
| EP | 0 605 497 | 3/1996 |
| EP | 0 724 877 | 8/1996 |
| EP | 0 757 911 | 2/1997 |
| FR | 2 617 047 | 3/1996 |
| GB | 1 527 638 | 10/1978 |
| GB | 2046094 | 9/1986 |
| HU | 211 580 B | 6/1995 |
| JP | 56167616 | 5/1980 |
| JP | 1502590 | 11/1980 |
| JP | 55141407 | 11/1980 |
| JP | 60208910 | 11/1980 |
| JP | 63233915 | 10/1985 |
| JP | 63502117 | 8/1987 |
| WO | WO 85/00011 | 1/1985 |
| WO | WO 87/04592 | 8/1987 |
| WO | WO 88/04924 | 7/1988 |
| WO | WO 91/04011 | 4/1991 |
| WO | WO 92/18105 | 10/1992 |
| WO | WO 94/20072 | 9/1994 |
| WO | WO 96/21439 | 7/1996 |
| WO | WO 96/24332 | 8/1996 |
| WO | WO 97/14407 | 4/1997 |
| WO | WO 98/07414 | 2/1998 |
| WO | WO 98/41239 | 9/1998 |
| WO | WO 99/29300 | 6/1999 |
| WO | WO 99/29316 | 6/1999 |
| WO | WO 99/49846 | 10/1999 |
| WO | WO 99/49848 | 10/1999 |
| WO | WO 00/10531 | 3/2000 |
| WO | WO 00/30616 | 6/2000 |
| WO | WO 00/40219 | 7/2000 |
| WO | WO 00/41682 | 7/2000 |
| WO | WO 01/30372 | 5/2001 |

OTHER PUBLICATIONS

Bangham et al., "Diffusion of Univalent Ions Across the Lamellae of Swollen Phospholipids", *J. Mol. Biol.* (1965) 13, pp. 238-252.

Huang et al., "Interaction of the N-terminus of Sterol Carrier Protein 2 with Membranes: Role of Membrane Curvature", *Biochem. J*, (1999) vol. 8, pp. 593-603.

Gregoriadis, Gregory, "The Carrier Potential of Liposomes in Biology and Medicine", *New Engl. J. Med.*, (1976) vol. 295, No. 13, pp. 704-710.
Cudd et al., "Liposomes Injected Intravenously into Mice Associate with Liver Mitochondria," *Biochem. Biophys Acta*, (1984) vol. 774, pp. 169-180.
Benz et al., "Electrical Capacity of Black Lipid Films and of Lipid Bilayers Made from Monolayers", *Biochem. Biophys. Acta*, (1975) vol. 394, pp. 323-334.
Goodman and Gillman's, "The Pharmacological Basis of Therapeutics," 7th Ed., *MacMillan Publishing Co.*, New York (1985) Chap. 15, p. 312.
Cherney, L.S., "Tetracaine Hydroiodide: A Long Lasting Local Anesthetic Agent for the Relief of Postoperative Pain", *Anesth. Analg.* (1963) vol. 42, No. 4, pp. 477-481.
Haynes et al., "Metal-Ligand Interactions in Organic Chemistry and Biochemistry", *B. Pullman and N. Goldblum (eds.)*, part 2, (1977), pp. 189-212.
Haynes et al., "Ultra-Long Duration Local Anesthesia Produced by Injection of Lecithin-coated Methoxyflurane Microdroplets", *Anesthesiology* (1985) vol. 63, No. 5, pp. 490-499.
Haynes et al., "Ultra-Long Duration Local Anesthesia Produced by Intra-Dermal Injection of Lecithin-Coated Methoxyflurane Microdroplets", *Proceed. Intern. Symp. Control. Rel. Bioact. Mater.*, (1987) vol. 14, pp. 293-294.
Kirkpatrick et al., "Local Anesthetic Efficacy of Methoxyflurane Microdroplets in Man," *Anesthesiology* (1987) 67(3A): A254.
Gennaro et al., "Sustained-Release Drug Therapy," *Remington's Pharmaceutical Sciences*, 17th Ed., (1985), p. 1645.
"Derived Diameters and Distribution Statistics," from an unknown web-site, 6 pages.
"Getting Started", Man 0106, Issue 1.0, (Jan. 1996), *Malvern Instruments Ltd.*, England, pp. 7.1-7.7.
Chulia et al., Powder Technology and Pharmaceutical Processes, (1994), pp. 66-67.
Herbert A. Leiberman and Leon Lachman, Eds., *Pharmaceutical Dosage Forms*, Tablets, vol. 1, (1980), p. 13.
Miyajima, Koichiro, "Role of Saccharides for the Freeze-Thawing and Freeze-Drying of Liposome", *Advanced Drug Delivery Review*, vol. 24, (1997), pp. 151-159.
Buchmuller et al., "Cryopel: Ein neus Verfahren zum Pelletieren und Frosten Biologischer Substrate," *Gas Aktuell*, 35, 1(989), pp. 10-13.
Wu et al., "Pharmacokinetics of Methoxyflurane After Its Intra-Dermal Injection as Lecithin-Coated Microdroplets," *Journal of Controlled Release*, (1989), vol. 9, pp. 1-12.
Pace et al., "Novel Injectable Formulations of Insoluble Drugs", *Pharmaceutical Technology*, vol. 23, No. 3, (Mar. 1999), pp. 116-134.
Rompp's Chemie Lexikon, 2 Aufl., Bd. 1, (1950), Stichwort, "Emulsion".
Bergmann, Ludwig, *Der Ultraschall*, 5 Aufl., (1949), Stuttgart, S. 551-564, 672f.
Lehninger Biochemistry, "The Molecular Basis of Cell Structure and Function", (1970) Chapter 10.
Guzman et al., Formation and Characterization of Cyclosporine-Loaded Nanoparticles, 1088 J. Pharm. Sci 82 (1993) No. 5 pp. 498-502.
Napper, Donald, "Polymeric Stabilizations of Colloidal Dispersions", (1983).
Muller et al., Emulsions and Nanosuspension, Chap. 9 (1998) p. 163.
Lourenco et al., "Steric Stabilization of Nanoparticles:size and Surface Properties", *Int. J. of Pharm.*, vol. 138 (1996), pp. 1-12.
Luckham, Paul F., "The Physical Stability of Suspension Concentrates with Particular Reference to Pharmaceutical and Pesticide Formulations", *Pestic Sci.*, 1989, vol. 25, pp. 25-34.
Calvor et al., Production of Microparticles by High Pressure Homogenization, *Pharm. Dev. Tech.*, 1998, vol. 3(3), pp. 297-205.
[LSP4]LA FUMA Polymery , "The Role of Water-soluble Polymers at the Solid/liquid Interface in the Mechanisms of Flocculation/stabilazation of Aqueous Colloidal Suspenaions", 1998 43 nr 2, pp. 104-108.
Seikmann et al., "Melt-homogenized Solid Lipid Nanparticles Stabilized by the Non-ionic Surfactant Tyloxapol"., *Pharm. Pharmacol Lett*, 1994, vol. 3, pp. 225-228.
Freitas et al., "Spray-drying of Solid Lipid Nanoparticles (SLNtm)," European Journal of Pharmaceuticals and Biopharmaceuticals, 46, 1998, pp. 145-151.
Kawashima et al., "Preparation of Powdered Phospholipid Nanospheres by Spray Drying in a Aqueous System with Sugars," Chem. Pharm. Bull., 40(7), 1992, pp. 1911-1916.

* cited by examiner

THERMOPROTECTED COMPOSITIONS AND PROCESS FOR TERMINAL STEAM STERILIZATION OF MICROPARTICLE PREPARATIONS

This application claims the benefit of U.S. Provisional Application No. 60/087,331, filed May 29, 1998.

BACKGROUND

Several compositions of micro- and nano-particle suspensions of water-insoluble or poorly water-soluble biologically active substances such as pharmaceutical agents, and methods to prepare such suspensions have been described in patent literature. These compositions use surfactant molecules as surface modifiers that associate on the surface of the micro- or nano-particles and inhibit the growth of their size. Such surface stabilized microparticles may be administered to elicit their pharmaceutical advantage by injectable or oral or other routes of administration.

Drug delivery systems utilizing microparticulate suspensions have been described in literature (D. H. Haynes, "Phospholipid-coated Microcrystals: Injectable Formulations of Water-Insoluble Drugs." U.S. Pat. Nos. 5,091,187 and 5,091,188). These suspensions are believed to be the first applications of the surface modified microparticulate aqueous suspension containing particles made up of a core of pure drug substances and stabilized with natural or synthetic bipolar lipids including phospholipids and cholesterol. Subsequently, similar delivery systems exploiting these principles have been described (G. G. Liversidge et al., "Surface Modified Drug Nanoparticles." U.S. Pat. No. 5,145,684 K. J. Illig and P. Sarpotdar, "Formulations Comprising Olin 10-G to Prevent Particle Aggregation and Increase Stability." U.S. Pat. No. 5,340,564 H. William Bosch et al., "Process for Preparing Therapeutic Compositions Containing Nanoparticles." U.S. Pat. No. 5,510,118) emphasizing the usefulness of the drug delivery approach utilizing particulate aqueous suspensions.

Sterilization of the submicron- to micron-sized particle suspension of the pharmaceutical agent is necessary for their parenteral administration. The preferred method of sterilization of pharmaceutical parenteral agents is terminal sterilization by autoclaving. It has been found that many surface modified submicron- to micron-sized particle suspensions undergo particle size growth during autoclaving. This is attributed to the release of the surfactant molecules from the small particle surface and its subsequent coagulation at autoclaving temperatures. The small particles that are devoid of the surfactants become unstabilized and undergo particle size growth by various mechanisms. The temperature at which such coagulation of surfactant molecules occur is known as the cloud point of that surfactant. It is believed that addition of cloud point modifiers, which are merely other surfactants, raises the cloud point of the primary surfactant and thereby maintaining the surface modifier coating on the nanoparticles during autoclaving. The cloud point modifier molecules described in majority of the published literature (U.S. Pat. No. 5,298,262 U.S. Pat. No. 5,336,507, and U.S. Pat. No. 5,340,564) are ionic surfactants, including charged phospholipids.

Successful terminal steam sterilization of phospholipid-stabilized emulsions and phospholipid-liposomes have been reported in literature [1-4]. However, examples of successful terminal steam sterilization of micron or submicron size particle suspensions of water insoluble or poorly soluble drugs, that contain only phospholipids as the surface modifier, have not been reported prior to the findings reported in the present invention.

DESCRIPTION OF THE INVENTION

Surprisingly, it was found that selected compositions of submicron- to micron-sized particulate suspension of water-insoluble or poorly water-soluble pharmaceutical agents containing a pharmaceutically acceptable water soluble polyhydroxy compound could be autoclaved without any marked increase of mean particle size.

Yet another surprising finding was that such compositions withstood the stresses that are usually known to promote particle size growth or flocculation or agglomeration. For instance, without any significant increase in particle size, the steam sterilized compositions could be shaken for several days, could withstand the stress due to cyclical storage at 40 and 5° C., repeated freezing and thawing, or severe sedimentation forces.

It was a further surprising finding that these compositions could be successfully lyophilized before or after steam sterilization. In addition, the lyophilized preparations could be reconstituted by addition of water to make an aqueous suspension having qualities similar to the original suspension.

These compositions did not use any surfactants that would require cloud point modifying molecules for protection against coagulation, flocculation, crystal growth, or particle size growth during the terminal steam sterilization process. The steam sterilizable formulations described in the present invention differ from those known in the art by the absence of surfactants which have a tendency to coagulate on steam sterilization, e.g., polyvinylpyrrolidone, and presence of "thermoprotecting excipients as well as other thermoprotecting conditions" as described below.

The present invention focuses on how the growth of particles can be prevented during and after terminal steam sterilization of micron and sub-micron sized particles of water insoluble or poorly soluble pharmaceutical agents due to certain types of agents defined here as "thermoprotecting agents", and selected processing conditions defined here as "thermoprotecting conditions".

The "thermoprotecting agents" and "thermoprotecting conditions" are characterized by their ability to restrict the increase in volume weighted mean diameter of the particulate suspension during and after terminal steam sterilization to a limit that the steam sterilized suspension can be injected by intravenous or other parenteral routes of administration without compromising the safety of the subject. A volume weighted mean diameter of up to about 3 μm is considered safe for intravenous injection. However, such a suspension should not contain more than 3000 particles of 10 μm or greater size and not more than 300 particles of 25 μm or greater size according to the USP particulate test criterion. We have thus defined the term "successful steam sterilization" as a process with which one can prepare formulations which do not contain particles of above specified diameter limits or preferably the volume weighted mean particle diameter of the suspension does not increase after steam sterilization by more than about two-times.

While the surface modifiers possibly adsorb to the freshly made surfaces of drug particles during the process of particle size reduction, and (a) convert the lipophilic drug surface to a hydrophilic surface that has increased stability, and (b) possibly modify the surface charge of the drug particle surfaces, the thermoprotecting agent and thermoprotecting conditions described herein help maintain the particle size distribution of the suspension during and after the terminal steam sterilization conditions.

Examples of suitable thermoprotecting agents include one or a combination of pharmaceutically acceptable water soluble polyhydroxy compounds that also act as tonicity modifiers, such as dextrose, sucrose, mannitol, sorbitol, dextran, trehalose, lactose. A detailed description or these agents may be found in Remington's Pharmaceutical Sciences, 18th Edition, 1990, Mack Publishing Co., PA; and Theory and Practice of Industrial Pharmacy, Lachman et al., 1986.

Suitable thermoprotecting conditions include absence of high ionic strength, particularly absence of high concentration of hydrogen or hydroxyl ions. Some other suitable thermoprotecting conditions include absence of agents such as polyethylene glycols, polyvinyl alcohol, polyvinylpyrrolidone, which themselves have a natural tendency to coagulate at high temperatures.

Without wishing to limit this invention to any particular theory, it is thought that some of the functions of the combination of surface active or non-surface active thermoprotecting agents and thermoprotecting conditions as they relate to this invention are:

To suppress the process of Ostwald Ripening during the cooling cycle of the terminal steam sterilization and therefore maintain the particle size, increase the storage stability, minimize sedimentation, and decrease the particle growth while lyophilization and reconstitution.

To enhance the association of surface modifier and the drug particles such that the protecting environment around the particles is maintained over a wide range of temperature and pressure as is prevalent during the terminal steam sterilization process.

To increase the interface compatibility between water-insoluble drug particles and the liquid.

To aid in orienting the surface modifiers' hydrophilic portion preferentially into the aqueous phase while the lipophilic portion remains strongly adsorbed to the surface of the water-insoluble drug particle as well as to enhance the stability of such orientation.

The process that can be used to produce these stable submicron and micron size particles include mixing the drug with phospholipid, other surfactants, thermoprotecting agents, and other ingredients followed by sonication, milling, homogenization, microfluidization, and antisolvent and solvent precipitation, spray drying of the solution in compressed normal or supercritical solvents.

Examples of some preferred water-insoluble drugs include antifungal agents, immunosuppressive and immunoactive agents, antiviral agents, antineoplastic agents, analgesic and antiinflammatory agents, antibiotics, antiepileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and, antiarrhythmics, antihypertensive agents, antineoplastic agents, hormones, and nutrients. A detailed description of these drugs may be found in Remington's Pharmaceutical Sciences, 18th Edition, 1990, Mack Publishing Co., PA.

EXAMPLES

Example 1

Table I summarizes some of the example compositions and observations. In Table I is displayed the amounts of drug substance (itraconazole), egg-phospholipid (surface modifier), and tonicity agents (various polyhydroxy compounds) used in making those preparations. These compositions do not require addition of so-called cloud point modifying agents to prevent egg-phospholipid separation and coagulation. The attributes of the suspensions made before and after terminal steam sterilization is also included in this table.

These preparations have been made by mixing the ingredients with appropriate amount of water, adjusting the pH with the required quantities of aqueous sodium hydroxide, and then subjecting the dispersion to high pressure homogenization or high pressure microfluidization at pressures in the range of 10000 psi 25000 psi. During the homogenization or microfluidization process the process fluid was cooled to maintain a temperature between 5-35° C. The finished product was filled in 5 or 10 mL borosilicate USP Type I glass vials. These vials were sealed under nitrogen atmosphere and subjected to terminal steam sterilization at 121° C. for 15 to 30 minutes.

Successfully terminally steam sterilized preparations of itraconazole, experiments 1-A through 1-G, are displayed in Table I. By the term "successfully terminally steam sterilized preparations" it is understood in this example that the volume weighted mean particle diameter of the suspension did not increase after steam sterilization by more than two-times. To demonstrate this, Table-I shows the ratio of post-autoclaving mean particle size to that before sterilization, which are within 1.04 to 1.18. The volume-weighted diameters of these suspensions have been determined with a Malvern Mastersizer Microplus, which utilizes a method based on the diffraction of light by the particulate suspension.

Formulations 1-A to 1-G described in Table-I are examples of successful steam sterilized products without any significant increase in particle size. Volume weighted mean diameters of the suspensions after terminal steam sterilization for the said formulations did not increase by more than a factor of two.

TABLE I

Examples of terminally steam sterilized Microparticle-Itraconazole suspensions and their pre- and post-sterilization attributes.

| | Formulation Number | | | | | | |
| --- | --- | --- | --- | --- | --- | --- | --- |
| | 1-A | 1-B | 1-C | 1-D | 1-E | 1-F | 1-G |
| Drug Amount, % | 2 | 5 | 10 | 9 | 9 | 9 | 10 |
| Lipoid E80, % | 0.5 | 1.1 | 3.5 | 2.7 | 2.7 | 2.7 | 2.0 |
| Other Additive* | TRE | TRE | TRE | DE38 | DE77 | LAC | MAN |
| Other Additive, % | 12 | 12 | 13 | 10 | 10 | 10 | 5.5 |
| Water | qs 100% | qs 100% | qs 100% | qs 100% | qs 100% | qs 100% | qs 100% |
| Drug:Lipid Ratio | 4:1 | 4.5:1 | 2.86:1 | 3.33:1 | 3.33:1 | 3.33:1 | 5:1 |

TABLE I-continued

Examples of terminally steam sterilized Microparticle-Itraconazole suspensions and their pre- and post-sterilization attributes.

| | Formulation Number | | | | | | |
|---|---|---|---|---|---|---|---|
| | 1-A | 1-B | 1-C | 1-D | 1-E | 1-F | 1-G |
| Pre-Sterilization Particle Size, μm | 1.07 | 1.01 | 0.9 | 1.30 | 1.30 | 1.31 | 0.75 |
| Post-Sterilization Particle Size, μm | 1.16 | 1.16 | 1.03 | 1.53 | 1.5 | 1.45 | 1.27 |
| Post- to Pre-Sterilization Particle Size Ratio | 1.08 | 1.14 | 1.14 | 1.18 | 1.15 | 1.11 | 1.69 |

*Symbols and sources of chemicals: Itraconazol (Wyckoff Chemical Co.);
TRE = Trehalose (Pfanstiehl, Waukegan, IL);
DE38 = Dextran-average molecular weight = 38,100 (Sigma, St. Louis, MO);
DE77 = Dextran-average molecular weight = 7,000 (Sigma, St. Louis, MO);
LAC = Lactose (BDH Inc., Toronto, Canada);
MAN = Mannitol (J. T. Baker, Phillipsburg, NJ);
GLY = glycerin.

Example 2

In Table II are presented the results of some negative control experiments. As a control experiment, an itraconazole formulation (2-A) without any thermoprotectant and surface modifier addition was attempted. The solid drug could not be dispersed in water. Major portion of the drug remained floating on the surface of water. Therefore, it could not be homogenized. It was found that addition of a surfactant was necessary that also acted as a wetting agent. This formulation could not be made possible without any surface modifier. Therefore, steam sterilization and particle size determinations were not attempted.

The formulation 2-B to 2-E were prepared by the method described in Example 1.

TABLE II

Examples f terminally steam sterilized Microparticle-Itraconazole suspensions and their pre- and post-sterilization attributes.

| Formulation Number | 2-A | 2-B | 2-C | 2-D | 2-E |
|---|---|---|---|---|---|
| Drug: Itraconazole | 10% | 10% | 2.5% | 8.1% | 8.1% |
| Lipoid E80 | 0% | 10% | 10% | 2.4% | 2.4% |
| Other Additives[1] | 0% | MAN: 5.5% | GLY: 2.5% | TRE: 12% MRJ: 2.0% | TRE: 12% PF68: 2.0% |
| Water | qs 100% | qs 100% | qs 100% | qs 100% | qs 100% |
| Drug:Lipid Ratio | NA | 1:1 | 0.25:1 | 3.4:1 | 3.4:1 |
| Pre-Sterilization Particle Size, μm | ND[2] | 0.59 | ND[4] | 0.86 | 0.86 |
| Post-Sterilization Particle Size, μm | ND[2] | ND[3] | ND[4] | 7.84 | 4.22 |
| Post- to Pre-Sterilization Particle Size Ratio | ND[2] | ND[3] | ND[4] | 9.1 | 4.9 |

Notes:
[1]Symbols and sources of chemicals: Itraconazol (Wyckoff Chemical Co.); Lipoid E80 (Lipoid gmbH); TRE = Trehalose (Pfanstiehl, Waukegan, IL); MRJ = Myrj52S (ICI Surfactants); PF68 = Pluronic F68 (BASF); MAN = Mannitol (J. T. Baker, Phillipsburg, NJ); GLY = glycerin.
[2]The solid drug could not be dispersed in water, therefore, it could not be homogenized. It was found that addition of a surfactant was necessary that also acted as a wetting agent. This formulation could not be made possible without any surface modifier. Therefore, steam sterilization and particle size determinations were not attempted.
[3]Formulation 2-B demonstrated flocculation or aggregation and significant quantity of scum formation on the surface of the autoclaved material which dispersed slowly on vigorous agitation.
[4]Particle size of the formulation 2-C, consisting of 2.5% glycerol as the tonicity modifier, showed highly unstable particle size and therefore terminal steam sterilization was not performed.

The formulation 2-B demonstrated flocculation or aggregation and significant quantity of scum formation on the surface of the autoclaved material, which dispersed slowly on vigorous agitation. It was thought that the flocculation or creaming on steam sterilization of formulation 2-B originated from an excessive amount of phospholipid. This formulation has a 1:1 ratio of drug to Lipoid E80, i.e., 10% w/w each. It is believed that excessive amount of phospholipid resulted in some sort of cross-linked structure during steam sterilization that induced flocculation and creaming.

Additionally, in presence of a large excess of the surfactants during the steam sterilization conditions the particle size growth may occur due to solubilization of the drug in the microstructures of surfactant molecules followed by recrystallization upon cooling. Such microstructures include minute quantities of micelles or liposomes in equilibrium with other structures formed with the surfactant molecules. The fraction of these microstructures would increase with increasing quantities of the surfactants. It was thus recognized that maintaining a proper amount of the surface modifier in the formulation was important in order to avoid the particle size growth upon terminal steam sterilization.

In general, terminal steam sterilization of the microparticle formulations was found to be successful by reducing the phospholipid to a minimum quantity (e.g., from ~10% w/w to about 2-5% w/w) that could allow an effective coating of the phospholipid on the drug-microparticle while avoiding the undesirable phospholipid structures considered to be responsible for large size cross-linked structures on steam sterilization. A drug to phospholipid ratio above about 3:1 seemed to give good result (formulations 1-A to 1-G of Example 1). When the drug to phospholipid ratio was brought down, e.g., from 5:1 in formulation 1-G (Example 1), to 1:1 in formulation 2-B, extensive flocculation or aggregation and significant quantity of scum formation on the surface of the autoclaved material was observed.

Particle size of the formulation 2-C, consisting of 2.5% glycerol as the tonicity modifier, was unstable and therefore terminal steam sterilization was not performed. This formulation had a large quantity of phospholipid compared to the drug, giving a low drug to phospholipid ratio of 0.25:1. In addition, this formulation employed 2.5% w/w glycerin as the tonicity modifier. It is believed that the unfavorable drug:phospholipid ratio and/or use of glycerin as the tonicity modifier caused the observed increase in the particle size of the formulation even without the heat stress of terminal steam sterilization.

Formulations 2-D and 2-E represent the effect of addition of certain commonly used surfactants. Surfactant Myrj-52S (polyethyleneglycol-40 sterate) was present at 2.0% in formulation 2-D in addition to 2.4% Lipiod E80 and 8.1% itraconazole. Similarly, surfactant Pluronic F68 (a Poloxamer) was present at 2.0% in formulation 2-E in addition to 2.4% Lipiod E80 and 8.1% itraconazole. Although the mean particle size of the preautoclaved suspension of both formulations 2-D and 2-E remained 0.86 μm, upon steam sterilization it increased tremendously to 7.84 and 4.22 μm, respectively. Both the formulations became highly viscous after steam sterilization. The formulations 2-D and 2-E display the post-to pre-sterilization particle size ratios of 9.1 and 4.9 respectively. This experiment demonstrates that addition of certain surfactants to Lipiod E80 containing Microparticle formulations results in a large growth of particle size.

Example 3

Preparation "C" (Microparticle-Itraconazole (10%)) of the example 1 was used for this experiment. Approximately 5 g of the preparation was placed in a vial and sealed under nitrogen. Freeze/thaw stress was given as follows. The vial contents were frozen by storing in few a freezer (approximately −20° C.) for at least 6 hours. The frozen sample was then thawed by placing the vial at room temperature for 0.5-1 hour. Particle size distribution of the thawed sample was measured by the method mentioned above. Appearance of the thawed sample was recorded. The vial was then again sealed under nitrogen for the next cycle of this experiment. The results of this experiment are summarized in Table III. The formulation has displayed a very good particle size stability upon the destabilizing stress of freeze/thaw conditions.

Example 4

A thermal cycling stress was given to the preparation "1-C" of example 1 by storing the formulation for approximately 24 hours in a refrigerator at about 4° C. and then in an incubator at about 40° C. for approximately 24 hours. The particle size was measured and appearance noted at the end of each cycle. This cycle was repeated. The results are given below in Table IV. The results indicate a very good stability of the particle size and appearance of the formulation on thermal cycling stress. The formulation remained stable for 4 cycles, after which the study was terminated.

TABLE III

Particle size stability f Microparticle-Itraconazole (10%) on freeze/thaw stress.

| | Volume Weighted Particle Size, μm | | | |
|---|---|---|---|---|
| Cycle # | Mean | 90 Percentile | 99.9 Percentile | Appearance |
| 0 | 1.04 | 1.60 | 2.52 | Homogeneous White Suspension |
| 1 | 1.04 | 1.60 | 2.52 | |
| 2 | 1.01 | 1.53 | 2.47 | |
| 3 | 1.01 | 1.52 | 2.44 | |
| 4 | 1.05 | 1.61 | 2.53 | |
| 5 | 1.02 | 1.52 | 2.44 | |
| 6 | 1.01 | 1.50 | 2.38 | |
| 7 | 1.02 | 1.54 | 2.41 | |
| 8 | 1.03 | 1.55 | 2.42 | |
| 9 | 1.02 | 1.53 | 2.44 | |
| 10 | 1.03 | 1.57 | 2.47 | |

TABLE IV

Particle size stability of Microparticle-Itraconazole (10%) on thermal cycling (4-40° C.) stress.

| | Volume Weighted Particle Size Distribution (μm) | | | |
|---|---|---|---|---|
| Cycle # | Mean | 90 Percentile | 99.9 Percentile | Appearance |
| 0 | 1.04 | 1.60 | 2.52 | Homogeneous White Suspension |
| 1 | 1.01 | 1.52 | 2.45 | |
| 2 | 1.02 | 1.56 | 2.47 | |
| 3 | 1.02 | 1.57 | 2.50 | |
| 4 | 1.03 | 1.59 | 2.76 | |

Example 5

Good stability on shaking stress has been also demonstrated (see Table V). The steam-sterilized formulation of example "1-C" was tested. Shaking stress was given as follows. The vial containing the formulation was placed horizontally on an orbital shaker and shaken at approximately 100 rpm. The vial was removed from the shaker daily for observation of the appearance. Particle size was measured every alternate day. The volume weighted mean particle size and its 90 as well as 99.9 percentile did not change significantly on shaking for 7 days. The study was terminated after 7 days.

TABLE V

Particle size stability of Microparticle-
Itraconazole (10%) on shaking stress

| Shaking Stress Time Point | Volume Weighted Particle Size (μm) | | | Appearance |
|---|---|---|---|---|
| | Mean | 90 Percentile | 99.9 Percentile | |
| Day 0 | 1.04 | 1.60 | 2.52 | Homogeneous White Suspension |
| Day 3 | 1.05 | 1.64 | 2.83 | |
| Day 5 | 1.10 | 1.77 | 3.28 | |
| Day 7 | 1.06 | 1.68 | 2.83 | |

Example 6

The long-term sedimentation behavior was assessed by a centrifugation experiment and the formulation quality was determined by particle sizing (Table VI). Preparation "1-C" of example 1 was tested. The formulation could not be sedimented by centrifuging for approximately 20 min at 3000-rpm. Significant sedimentation was observed by increasing the centrifugation speed to approximately 5000 and 6000 rpm for another 20 min., however this sediment was resuspendable with some difficulty upon shaking. Resuspendibility was assessed as: Easy: Sedimented suspension became visually homogeneous on shaking gently by hand. Moderate: Sedimented suspension became visually homogeneous on vigorous hand shaking. Difficult: Vortexing required for the sedimented suspension to make visually homogeneous.

There was no increase in particle size upon such sedimentation. In addition, agglomeration or flocculation was not observed in optical microscopy. Average particle size by the optical microscopy agreed with that by Malvern Mastersizer.

Table VI

Stability of Microparticle-Itraconazole (10%) on sedimentation stress

| Centrifuging Condition | | | | Volume Weighted Particle Size (μm) | | |
|---|---|---|---|---|---|---|
| Speed (rpm) | Duration (min) | Sedimentation | Resuspendibility | Mean | 90 Percentile | 99.9 Percentile |
| Before Centrifugation | | None | NA* | 1.05 | 1.58 | 2.48 |
| 1000 | 5 | None | ND* | ND | ND | ND |
| 1500 | 10 | None | NA | ND | ND | ND |
| 2000 | 15 | Little | Easy | 1.02 | 1.51 | 2.39 |
| 3000 | 15 | Little | Moderate | 0.99 | 1.47 | 2.20 |
| 5000 | 15 | Significant | Difficult | 0.97 | 1.43 | 2.19 |
| 6000 | 15 | Significant | Difficult | 0.99 | 1.46 | 2.17 |

*NA = Not Applicable; ND = Not Determined.

Example 7

Preparation "1-C" (Microparticle-Itraconazole (10%)) of the Example 1 was used for this experiment. Approximately 5 g of the unautoclaved product was placed in a glass vial and lyophilized. The vials that were terminally steam sterilized were also lyophilized. The lyophilized material was an off-white cake. The lyophilized cake was easily reconstituted with water by 4-5 gentle inversions of the vial into a homogenous white suspension. The appearance and particle size of the original suspension and that of lyophilized and reconstituted preparation is presented in Table VII. Both the unautoclaved and autoclaved formulations display good particle size stability upon lyophilization and reconstitution.

Example 8

The formulations and their attributes of this example are given in Table VIII. These formulations were prepared by the methods of Example 1. In the microparticle-cyclosporine formulation 8-A, polyhydroxy compound acting as thermoprotectant or tonicity modifier was not added into the premix. The particle size reduction profile was found to be very inefficient. The volume weighted mean particle diameter of the suspension was about 4 micrometers at the end of homogenization. This suspension was steam sterilized at 121° C. for 15 minutes that resulted in a heavy coagulated mass of the solid particles of several millimeters. Almost all of the drug substance was seen sedimented leaving behind a clear supernatant.

TABLE VII

Particle size stability upon lyophilization and reconstitution
of a Microparticle-Itraconazole (10%) Suspension

| Formulation Condition | Appearance | Volume Weighted Particle Size (μm) | | |
|---|---|---|---|---|
| | | Mean | 90 Percentile | 99.9 Percentile |
| Unsterilized Suspension Before Lyophilization | Homogeneous White Suspension | 0.9 | 1.31 | 2.08 |
| Unsterilized Lyophilized and Reconstituted Suspension | Homogeneous White Suspension | 1.00 | 1.60 | 2.56 |
| Sterilized Suspension Before Lyophilization | Homogeneous White Suspension | 1.03 | 1.59 | 2.51 |

TABLE VII-continued

Particle size stability upon lyophilization and reconstitution
of a Microparticle-Itraconazole (10%) Suspension

| Formulation Condition | Appearance | Volume Weighted Particle Size (μm) | | |
|---|---|---|---|---|
| | | Mean | 90 Percentile | 99.9 Percentile |
| Sterilized Lyophilized and Reconstituted Suspension | Homogeneous White Suspension | 1.10 | 1.71 | 2.51 |

TABLE VIII

More examples of terminally steam sterilized microparticle formulations.

| Formulation Number | 8-A | 8-B |
|---|---|---|
| Drug | Cyclosporine | Cyclosporine |
| Drug Amount, % | 10 | 10 |
| Trehalose, % | None | 12 |
| Lipoid E80, % | 3.0 | 3.0 |
| Pre-Sterilization Particle Size, μm | ~4 | 0.72 |
| Post-Sterilization Particle Size, μm | Large Particles by Visual Inspection | 1.03 |
| Ratio of Post- and Pre-Sterilization Particle Sizes | Much greater than 2 | 1.43 |

Premix of formulation 8-B contained trehalose in addition to the components of example 8-A. The homogenization process of this formulation was interrupted in the midway by allowing to stand overnight under nitrogen atmosphere at ambient temperature. The homogenization was completed the next day. Efficient particle size reduction to a volume weighted mean diameter of 0.72 micrometers was observed. In addition, this formulation could be successfully steam sterilized at 121° C. for 15 minutes with an acceptable increase in the particle size to approximately 1.03, an increase by a factor of only 1.43. It is believed that the presence of the polyhydroxy compound, trehalose, allowed the efficient particle size reduction. The formulation could withstand the heat stress of autoclaving without a large increase in the particle size.

Example 9

Some example formulations containing Alfaxalone and their pre and post steam sterilization attributes are shown in Table IX. These formulations were prepared by the methods of Example 1.

TABLE IX

Examples of terminally steam sterilized Microparticle-Alfaxalone formulations.

| Formulation Number | 9-A | 9-B | 9-C |
|---|---|---|---|
| Drug Amount, % | 3.0 | 3.0 | 3.0 |
| Lipoid E80, % | 2.0 | 2.0 | 1.0 |
| DSPC, %* | 1.0 | 1.0 | 0.5 |
| DMPG, %** | 0.2 | 0.2 | 0.1 |
| Dextran, % | 20 | — | 20 |
| Sodium Chloride, M | — | — | — |
| Water | qs 100% | qs 100% | qs 100% |
| Pre-Sterilization Mean Particle Size, μm | 1.38 | 1.38 | 1.42 |
| Post-Sterilization Mean Particle Size, μm | 2.95 | 5.24 | 2.71 |
| Ratio of Post- and Pre-Sterilization Mean Particle Sizes | 2.1 | 3.8 | 1.9 |

*DSPC = disteroylphosphatidyl choline
**DMPG = dimyristoylphosphatidyl glycerol

Formulation, 9-A, which has a combination of phospholipids (Lipoid E80, DSPC and DMPG) and dextran as the thermoprotectant, demonstrates about 2-fold increase in particle size upon steam sterilization by heating at 121° C. for 15 min. On the other hand, formulation 9-B, which has composition similar to that of 9-A except the absence of dextran, shows a much higher mean particle size (5.24 μm) and the ratio of post- and pre-sterilization mean particle sizes of 3.8.

Thus presence of dextran in formulation 9-A has improved the particle size stabilization over that of formulation 9-B. Formulation 9-C is very similar to the formulation 9-A except slightly different amounts of surface modifiers. In this formulation also the particle size increase has been limited to about a factor of two. It has a mean particle size of 2.71 μm and the ratio of post- and pre-sterilization mean particle sizes of only 1.9.

In addition to the example compositions mentioned above, the formulations of this invention may additionally contain suitable amount of pH buffering salts and pH adjusting agents such as sodium hydroxide and/or pharmaceutically acceptable acids. It is known to those skilled in the art of handling the phospholipids that at pH lower than 5 and higher than 9 the phospholipid molecules undergo extensive hydrolysis. Therefore, the pH of the suspension was usually adjusted to within this range prior to homogenization, and if necessary readjusted prior to steam sterilization.

While the invention and the examples have been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the following claims.

REFERENCES

1. "Cyclosporin emulsions", Parikh, Indu; and Mishra, Awadhesh; U.S. Pat. No. 5,660,858, 1997.
2. "Composition for enhancing the administration of pharmacologically active agents", Wretlind, Karl A. J.; Ljungberg, Stellan; Hakansson, Ivan; Ajaxon, Bengt M.; USRE #032393, 1987.
3. "Sterilization of liposomes by heat treatment" by Zuidam, Nicolaas J.; Lee, Stephan S. L.; and Crommelin, Daan J. A.; *Pharmaceutical Research* 10:1592-1596, 1993.
4. "Liposomes" Klaveness, Jo; Berg, Arne; Jacobsen, Trond Vegard; Rongved, Pal; Ege, Thorfinn; Kikuchi, Hiroshi; Yachi, Kiyoto; U.S. Pat. No. 5,676,928, 1997.

What is claimed is:

1. An injectable aqueous terminally steam sterilized composition consisting essentially of a particulate suspension of a water insoluble or poorly soluble biologically active substance wherein the particles in the suspension have a volume weighted mean particle size of up to 3 μm, with not more than 3000 particles of a size of 10 μm or greater and not more than 300 particles of a size of 25 μm or greater, and said particles are surface stabilized with one or more phospholipid surface modifiers and a pharmaceutically acceptable amount of a water soluble polyhydroxy thermoprotecting agent selected from the group consisting of trehalose, lactose, dextrose, sorbitol, dextran, mannitol and mixtures thereof, wherein said thermoprotecting agent is present in an amount effective to restrict an increase in volume weighted mean diameter of said suspension during and after terminal steam sterilization, wherein the ratio of said active substance to said phospholipid surface modifier is from about 3:1 to about 5:1 and the amount of said phospholipid surface modifier is in the range from about 0.2% w/w to about 5.0% w/w, wherein said composition is devoid of surfactants that require during terminal steam sterilization elevation of their cloud point temperature by addition of a cloud point modifier, said composition being devoid of surfactant additives which coagulate on steam sterilization.

2. An injectable aqueous terminally steam sterilized composition consisting essentially of a particulate suspension of a water insoluble or poorly soluble biologically active substance
wherein the particles in the suspension have a volume weighted mean particle size of up to 3 μm, and
said particles are surface stabilized with one or more phospholipid surface modifiers, and a pharmaceutically acceptable amount of a water soluble polyhydroxy thermoprotecting agent, wherein said thermoprotecting agent is present in an amount effective to restrict an increase in volume weighted mean diameter of said suspension during and after terminal steam sterilization,
wherein (i) the ratio of said drug substance to said surface modifier is about 3:1 to about 5:1,
(ii) the amount of said surface modifier is in the range from about 0.2% w/w to about 5.0% w/w, and
(iii) wherein said composition is devoid of surfactants that require during terminal steam sterilization elevation of their cloud point temperature by addition of a cloud point modifier and is devoid of surfactant additives which coagulate on steam sterilization.

3. The composition according to claim 1 or claim 2, wherein the suspension also includes a nonsurfactant additive to adjust osmotic pressure.

4. The composition according to claim 1 or claim 2, wherein the suspension is diluted with water for parenteral administration.

5. The composition according to claim 2, wherein the suspension further comprises a pharmaceutical excipient for ophthalmic, peroral, or transdermal administration of the water insoluble or poorly soluble drug substance.

6. The composition according to claim 1, wherein the active substance is an antifungal agent.

7. The composition according to claim 6, wherein the antifungal agent is itraconazole.

8. The composition according to claim 1, wherein the active substance is an immunosuppressive agent.

9. The composition according to claim 1, wherein the active substance is a sterol.

10. The composition according to claim 9, wherein the sterol is alfaxalone.

11. A lyophilized or spray dried powder prepared from the composition according to claim 2.

12. The composition according to claim 2, wherein the water-insoluble or poorly water soluble drug substance is suitable for either immediate release or sustained release delivery of said drug substance by parenteral administration.

13. The composition according to claim 12, wherein the parenteral administration is intramuscular, intravenous, or subcutaneous administration.

14. The composition according to claim 8, wherein the immunosuppressive agent is a cyclosporin.

15. The composition according to claim 1, wherein said composition consists of
said particles of said water insoluble or poorly soluble biologically active substance,
said one or more phospholipid surface modifiers, and
said polyhydroxy thermoprotecting agent.

16. The composition according to claim 2, wherein said composition consists of
said drug substance,
said one or more phospholipid surface modifiers, and
said polyhydroxy thermoprotecting agent.

17. The composition of claim 1, wherein the phospholipid surface modifier is egg phospholipid, or soy phospholipid.

18. The composition of claim 2, wherein the polydroxy thermoprotecting agent is selected from the group consisting of trehalose, lactose, dextrose, sorbitol, dextran, and mixtures thereof.

19. The composition of claim 2, wherein the phospholipid surface modifier is egg phospholipid, or soy phospholipid.

20. The aqueous suspension of claim 3, wherein the suspension lacks glycerol.

21. The aqueous suspension of claim 4, wherein the suspension lacks glycerol.

22. The composition of claim 1, wherein the composition is under nitrogen in a sealed vial.

23. The composition of claim 1, wherein the composition is under nitrogen in a sealed vial.

* * * * *

UNITED STATES PATENT AND TRADEMARK OFFICE
CERTIFICATE OF CORRECTION

| | |
|---|---|
| PATENT NO. | : 8,415,329 B1 |
| APPLICATION NO. | : 09/321766 |
| DATED | : April 9, 2013 |
| INVENTOR(S) | : Awadhesh K. Mishra |

It is certified that error appears in the above-identified patent and that said Letters Patent is hereby corrected as shown below:

In the claims:

At column 14, line number 39, in claim 23, please correct claim "1" to read claim "2".

Signed and Sealed this
Fourth Day of June, 2013

Teresa Stanek Rea
*Acting Director of the United States Patent and Trademark Office*